United States Patent
Agarwal et al.

(10) Patent No.: US 10,413,525 B2
(45) Date of Patent: *Sep. 17, 2019

(54) DULOXETINE SPRINKLES

(71) Applicant: Sun Pharmaceutical Industries, Ltd., Mumbai, Maharashtra (IN)

(72) Inventors: Ravindra Agarwal, Udaipur (IN); Tarun Singhal, Bharatpur (IN); Ravi Kochhar, Haryana (IN)

(73) Assignee: Sun Pharmaceutical Industries Limited, Mumbai, Maharashtra (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/805,932

(22) Filed: Nov. 7, 2017

(65) Prior Publication Data

US 2018/0161306 A1 Jun. 14, 2018

Related U.S. Application Data

(63) Continuation of application No. 15/486,670, filed on Apr. 13, 2017, now Pat. No. 9,839,626.

(30) Foreign Application Priority Data

Dec. 14, 2016 (IN) .............................. 201611042630

(51) Int. Cl.
| | | |
|---|---|---|
| A61K 9/50 | (2006.01) |
| A61K 31/381 | (2006.01) |
| A23L 33/10 | (2016.01) |
| A61K 9/16 | (2006.01) |

(52) U.S. Cl.
CPC ............ *A61K 31/381* (2013.01); *A23L 33/10* (2016.08); *A61K 9/1629* (2013.01); *A61K 9/1641* (2013.01); *A61K 9/1652* (2013.01); *A61K 9/1676* (2013.01); *A61K 9/5021* (2013.01); *A61K 9/5078* (2013.01); *A61K 9/5084* (2013.01); *A23V 2002/00* (2013.01)

(58) Field of Classification Search
CPC .. A61K 9/5021; A61K 9/5078; A61K 9/5084; A61K 9/1676
See application file for complete search history.

(56) References Cited

U.S. PATENT DOCUMENTS

| | | | |
|---|---|---|---|
| 5,508,276 A * | 4/1996 | Anderson | ............ A61K 31/381 424/458 |
| 8,455,667 B2 | 6/2013 | Sesha | |
| 8,513,439 B2 | 8/2013 | Sesha | |
| 8,758,779 B2 | 6/2014 | Mate et al. | |
| 2010/0040680 A1 | 2/2010 | Lai et al. | |

FOREIGN PATENT DOCUMENTS

| | | |
|---|---|---|
| WO | WO-2007/139886 A2 | 12/2007 |
| WO | WO-2009/004649 A2 | 1/2009 |
| WO | WO-2010/078878 A1 | 7/2010 |

OTHER PUBLICATIONS

European Extended Search Report dated May 15, 2018 for European Patent Application No. 17207371.0 (7 pages).
"Substance use disorder comorbidity in major depressive disorder: an exploratory analysis of the Sequenced Treatment Alternatives to Relieve Depression cohort", Lori L. Davis et al, Comprehensive Psychiatry 46 (2005) 81-89.
"Drinking alcohol during antidepressant treatment—a cause for concern"; David B. Menkes et al; The Pharmaceutical Journal Dec. 20, 2011.
"Treatment of the Depressed Alcoholic Patient"Jeffrey J. DeVido et al; Curr Psychiatry Rep. Dec. 2012; 14(6): 610-618.
"Formulation and Stabilization of Duloxetine Hydrochloride Delayed Release Pellets with the Aid Non Ionic Barrier Layer" Raja Subburayalu et al., IOSR Journal of Pharmacy (e)-ISSN: 2250-3013, (p)-ISSN: 2319-4219.

* cited by examiner

*Primary Examiner* — Carlos A Azpuru
(74) *Attorney, Agent, or Firm* — Goodwin Procter LLP

(57) ABSTRACT

The present invention relates in part a to multiparticulate sprinkle dosage form comprising duloxetine or a pharmaceutically acceptable salt thereof, having higher acid resistance as compared to commercially available delayed release formulations. It further relates to various methods of administering the said multiparticulate sprinkle dosage forms.

7 Claims, No Drawings

DULOXETINE SPRINKLES

RELATED APPLICATIONS

This application is a continuation application of U.S. patent application Ser. No. 15/486,670 filed Apr. 13, 2017, which claims priority to Indian patent application number 201611042630, filed Dec. 14, 2016, each of which is hereby incorporated by reference in its entirety.

FIELD OF THE INVENTION

The present invention relates in part to a multiparticulate sprinkle dosage form comprising duloxetine or a pharmaceutically acceptable salt thereof, having, for example, significantly higher acid resistance as compared to delayed release formulations. It further relates to various methods of administering the said multiparticulate sprinkle dosage forms.

BACKGROUND

Duloxetine is a selective serotonin and norepinephrine reuptake inhibitor (SSNRI), chemically known as (+)-N-methyl-3-(1-naphthalenyloxy)-3-(2-thienyl)propan-1-amine). Duloxetine is an acid labile drug and degrades in acidic environment of gastrointestinal tract (GIT). Acid hydrolysis of its ether linkage results in the formation of 1-naphthol, which is known to be toxic and causes several side effects. At pH 1.0, which is achieved under fasting conditions in vivo, 50% of drug in the dosage is hydrolyzed to 1-naphthol; at pH of 2.0, 10% of the drug degrades to 1-naphthol in one hour, and at a pH of 4.0, 10% degradation would take up to 63 hours. This acid sensitive compound is therefore available as enteric coated dosage form to protect it from degradation.

Duloxetine is commercially available in USA as delayed release capsules marketed under the brand name Cymbalta®. These capsules contain enteric coated duloxetine hydrochloride pellets encapsulated in a hard gelatin capsule. Some pediatric and geriatric patients have difficulties in swallowing such conventional dosage forms (e.g., capsules, and commercially available formulations of duloxetine are not suitable for administration to patients who have difficulties in swallowing. Further, dysphagic patients and patients with G-tubes or NG-tubes cannot swallow the conventional oral dosage forms leading to poor patient compliance.

Further, since duloxetine is an acid labile drug, it cannot be given as liquid or chewable dosage form generally used for the patients with these difficulties. It is not advisable to take duloxetine as an acid labile drug in liquid form, as it may lead to the formation of toxic degradation products in the presence of acid. Therefore there further exists a need to formulate gastro resistant compositions having high acid resistance, especially in patients with conditions that may slow gastric emptying (e.g., some diabetics). For example, delay in gastric emptying may expose the composition to the acidic environment for prolonged period of time, thus affecting the stability of enteric coating and release of duloxetine in the stomach, wherein duloxetine undergo acid hydrolysis leading to formation of 1-naphthol, a toxic impurity.

U.S. Pat. No. 5,508,276 discloses enteric coated pellets of duloxetine coated with hydroxypropylmethyl cellulose acetate succinate (HPMCAS) as the enteric coating agent. The compositions disclosed are to be swallowed whole. U.S. Pat. No. 8,758,779 discloses duloxetine powder for oral suspension and taste masked granules to be reconstituted with water at the time of administration. U.S. Pat. Nos. 8,455,667 and 8,513,439 disclose an oral liquid composition comprising duloxetine and a buffering agent. The composition is in the form of a powder for suspension in a liquid or in the form of aqueous solution/suspension.

Thus, there exists a need in the art for an alternate gastro resistant duloxetine composition suitable for administration to pediatrics, geriatrics and other patients having difficulty in swallowing a well as suitable for administration to patients with enteral feeding tube in place leading to improved patient compliance, as well as a duloxetine formulation having a higher acid resistance with stability for longer periods as compared to available delayed release capsules.

SUMMARY

The present disclosure relates in part to a multiparticulate sprinkle dosage form comprising enteric coated discrete units of duloxetine hydrochloride that can be mixed with or sprinkled on food and swallowed intact with the food. The dosage forms have higher acid resistance as compared to existing delayed release capsules but at the same time are bioequivalent. The multiparticulate sprinkle dosage form of the present invention may further be suitable for administration via nasogastric tube (NG) or via other enteral feeding tube and has high acid resistance stability after passage through NG tube as well. However, it presents a challenge for the present inventors to formulate a sprinkle dosage form of an acid labile drug.

DETAILED DESCRIPTION OF THE INVENTION

A first aspect of the present invention provides a multiparticulate sprinkle dosage form comprising duloxetine or a pharmaceutically acceptable salt thereof, wherein the sprinkle dosage form releases not more than 10% of 1-naphthol impurity after 6 hours when placed in 1000 mL of 0.1N HCl at 100 rpm in USP dissolution apparatus I.

According to one embodiment of this aspect, the multiparticulate sprinkle dosage form releases not more than 5% of 1-naphthol impurity after 4 hours when placed in 1000 mL of 0.1N HCl at 100 rpm in USP dissolution apparatus I.

According to another embodiment of this aspect, the multiparticulate sprinkle dosage form releases not more than 10% of total duloxetine after 4 hours when placed in 1000 mL of 0.1N HCl at 100 rpm in USP dissolution apparatus I.

According to another embodiment of this aspect, the multiparticulate sprinkle dosage form releases not more than 20% of duloxetine after 4 hours when placed in 1000 mL of 0.1N HCl at 100 rpm in USP dissolution apparatus I.

According to another embodiment of this aspect, a disclosed multiparticulate sprinkle dosage form of duloxetine or a pharmaceutically acceptable salt thereof has higher acid resistance as compared to existing duloxetine delayed release capsules available under the brand name Cymbalta®, i.e., capsules of duloxetine HCl having an enteric layer of hydroxypropyl methylcellulose acetate succinate.

According to another embodiment of this aspect, the multiparticulate sprinkle dosage form is bioequivalent to the existing duloxetine delayed release capsules that have an enteric layer of hydroxypropyl methylcellulose acetate succinate.

According to another embodiment of this aspect, the multiparticulate sprinkle dosage form when administered after sprinkling on soft food has enhanced oral bioavailability as compared to the marketed duloxetine delayed release capsules available under the brand name Cymbalta®.

According to one embodiment of this aspect, the multiparticulate sprinkle dosage form is present in the form of tablets, capsules, sachet or granules.

According to another embodiment of this aspect, the multiparticulate sprinkle dosage form comprises discrete units (core subunits) coated with an enteric polymer.

According to another embodiment of this aspect, the discrete unit or the multiparticulate is present in the form of pellets, beads, particles, granules, or minitablets. According to another embodiment of this aspect, the discrete unit comprises inert cores coated with the drug layer.

According to another embodiment of this aspect, the multiparticulate sprinkle dosage form contains duloxetine or pharmaceutically acceptable salts thereof in an amount of not less than 10%, preferably not less than about 15%, more preferably in an amount of about 20% by weight of the dosage form.

According to another embodiment, the enteric polymer is present in an amount of not less than about 75% by weight based on the weight of the enteric coating.

According to another embodiment, the enteric layer is present in an amount of about 15% to about 30% by weight based on the weight of the core subunit without the enteric coat.

According to another embodiment, the enteric layer is present in an amount of about 18% to about 25% by weight based on the weight of the core subunit without the enteric coat.

According to another embodiment of this aspect, the multiparticulate sprinkle dosage form comprises a cushioning agent.

According to another embodiment of this aspect, the cushioning agent is present in an amount of not less than 2% and not more than 20% based on the weight of the enteric coated pellet.

According to another embodiment of this aspect, the multiparticulate sprinkle dosage form is resistant to alcohol induced dose dumping.

According to another embodiment, the multiparticulate sprinkle dosage form exhibits dissolution of not more than 20% within 45 minutes, not more than 60% within 60 minutes, not more than 75% of duloxetine within 75 minutes, when placed in 1000 mL of 0.1N HCl and 20% alcohol in USP apparatus I.

According to another embodiment of this aspect, the multiparticulate sprinkle dosage form can be placed in contact with soft food before administration without affecting the stability of the enteric coating.

According to another embodiment of this aspect, the multiparticulates when sprinkled on soft food are stable for at least 60 minutes.

According to one embodiment of this aspect, the multiparticulates when sprinkled on soft food having pH less than or equal to 5 are stable for about 90 minutes.

According to another embodiment of this aspect, the multiparticulates when sprinkled on soft food having pH more than 5 at e.g., 25° C. or 37° C. are stable for about 60 minutes.

According to another embodiment of this aspect, the multiparticulate sprinkle dosage form is suitable for administration in intact form. According to one embodiment of this aspect, the multiparticulate sprinkle dosage form is suitable for administration to a patient via a feeding tube. According to another embodiment of this aspect, the multiparticulate sprinkle dosage form has higher acid resistance stability after recovery through a feeding tube.

For example, provided herein is a multiparticulate sprinkle dosage form comprising a plurality of discrete units, wherein each unit comprises: a drug layered subunit comprising an inert core, and a drug layer surrounding the inert core, wherein the drug layer comprises duloxetine or a pharmaceutically acceptable salt thereof, about 18% to about 25% weight percent (e.g., about 23% weight percent) of an enteric coating surrounding the drug layered subunit, based on the weight of the drug layered subunit without the enteric coating, wherein the enteric coating comprises 75% to about 99% by weight of an enteric polymer (e.g., hydroxypropylmethyl cellulose phthalate), based on the weight of the enteric coating; and a finishing layer over the enteric coating; wherein the sprinkle dosage form releases not more than 10% of 1-naphthol impurity after 6 hours when placed in 1000 mL of 0.1N HCl at 100 rpm in USP dissolution apparatus. Such a multiparticulate sprinkle dosage form may release not more than 5% of 1-naphthol impurity after 4 hours when placed in 1000 mL of 0.1N HCl at 100 rpm in USP dissolution apparatus I and/or releases not more than 10% of total duloxetine after 4 hours when placed in 1000 mL of 0.1N HCl at 100 rpm in USP dissolution apparatus I.

The discrete units of such disclosed multiparticulate sprinkle dosage form can be placed, for example, in contact with soft food before administration for at least 60 minutes without affecting the stability of the enteric coating.

Discrete units may be in a form selected from the group consisting of pellets, beads, particles, granules, and minitablets and the like.

Disclosed multiparticulate sprinkle dosage forms having discrete units, as disclosed herein, after 90 minutes of contact with soft food having a pH less than or equal to 5 (at e.g., 25° C.), may release not more than 2% of 1-naphthol after 2 hours when placed in 1000 mL of 0.1N HCl in USP apparatus I, and/or after 60 minutes contact with soft food having a pH more than 5 (at e.g., 25° C.), release not more than 4% of the 1-naphthol impurity after 2 hours, when placed in 1000 mL of 0.1N HCl in USP apparatus I; and/or discrete units after 60 minutes contact with soft food having a pH more than 5, release not more than 10% of the total duloxetine after 2 hours, when placed in 1000 mL of 0.1N HCl in USP apparatus I.

Disclosed multiparticulate sprinkle dosage forms having discrete units, as disclosed herein, when exposed to 50 mL water for 60 minutes in a syringe, and then passed through a 12 French nasogastric tube into 925 mL dissolution medium of 0.1N HCl, followed by flushing with additional 25 mL water, release not more than 5% of 1-naphthol impurity after 2 hours when then placed in 1000 mL of 0.1 N HCl at 100 rpm in USP apparatus I, and/or when exposed to 50 mL water for 60 minutes in a syringe, and then passed through a 12 French nasogastric tube into 925 mL dissolution medium of 0.1N HCl, followed by flushing with additional 25 mL water, release not more than 10% of total duloxetine after 2 hours when then placed in 1000 mL of 0.1 N HCl at 100 rpm in USP apparatus I.

Provided herein, for example, is a multiparticulate sprinkle dosage form comprising a plurality of pellets each comprising: a drug layered pellet comprising an inert core, and a drug layer surrounding the inert core comprising duloxetine or a pharmaceutically acceptable salt thereof, about 18 to about 25 (e.g., 23) weight percent of an enteric coating surrounding the drug layered subunit, based on the weight of the drug layered subunit without the enteric coating, wherein the enteric coating comprises an enteric polymer; and a finishing layer; wherein the sprinkle dosage form releases not more than 10% of 1-naphthol impurity after 6 hours when placed in 1000 mL of 0.1N HCl at 100 rpm in USP dissolution apparatus I. For example, in some embodiments, the enteric polymer of disclosed discrete units is hydroxypropylmethyl cellulose phthalate and the finishing layer comprises polyethylene glycol 6000.

Provided herein, for example, is a multiparticulate sprinkle dosage form to a patient, comprising a plurality of pellets, each pellet comprising:
a core subunit comprising:
    a drug layered pellet comprising an inert sphere coated with a drug layer, wherein the drug layer comprises dulexotine hydrochloride and hydropropylmethyl cellulose, and
    a subcoating comprising hydroxypropylmethylcellulose, wherein the subcoating covers the drug layered pellet;
an enteric coating comprising about 75 weight percent or more hydroxypropylmethylcellulose phthalate, based on the weight of the enteric coating, wherein the enteric coating covers the subcoating; and a
a finishing layer comprising PEG6000, wherein the dosage form contains one of: 67.3 mg of dulexotine hydrochloride, equivalent to 60 mg dulexotine free base, 22.4 mg of dulexotine hydrochloride, equivalent to 20 mg dulexotine free base, or 33.7 mg dulexotine hydrochloride, equivalent to 30 mg dulexontine free base.

In a second aspect of the present invention provides a multiparticulate sprinkle dosage form comprising duloxetine or a pharmaceutically acceptable salt thereof, wherein the dosage form comprises multiparticulates coated with a cushioning agent.

According to one embodiment of this aspect, the multiparticulate sprinkle dosage form comprises: (a) an inert core, (b) optionally an inner seal coat, (c) a drug layer, (d) optionally a sub coating layer, (c) an enteric coating layer, (f) optionally a finishing layer. According to another embodiment of this aspect, the cushioning agent is present in the finishing layer. According to another embodiment of this aspect, the cushioning agent is present in an amount of not less than 2% and not more than 20% based on the total weight of the dosage form.

According to another embodiment of this aspect, the multiparticulate sprinkle dosage form has higher acid resistance as compared to the marketed duloxetine delayed release capsules available under the brand name Cymbalta®.

A third aspect of the present invention provides a multiparticulate sprinkle dosage form comprising duloxetine or a pharmaceutically acceptable salt thereof, wherein the dosage form can be placed in contact with soft food before administration for at least 60 minutes without affecting the stability of the enteric coating.

According to one embodiment of this aspect, the multiparticulates when sprinkled on soft food having pH less than or equal to 5 are stable for about 90 minutes.

According to another embodiment of this aspect, the multiparticulates when sprinkled on soft food having pH more than 5 are stable for about 60 minutes.

According to another embodiment of this aspect, the multiparticulates when subjected to acid resistance test after 90 minutes of contact with soft food having pH less than or equal to 5, release not more than 2% of 1-naphthol impurity after 2 hours, when placed in 1000 mL of 0.1N HCl in USP apparatus I.

According to another embodiment of this aspect, the multiparticulates when subjected to acid resistance test after 60 minutes contact with soft food having pH more than 5, release not more than 4% of the 1-naphthol impurity after 2 hours, when placed in 1000 mL of 0.1N HCl in USP apparatus I.

According to another embodiment of this aspect, the multiparticulates when subjected to acid resistance test after 60 minutes contact with soft food having pH more than 5, release not more than 10% of the total duloxetine after 2 hours, when placed in 1000 mL of 0.1N HCl in USP apparatus I.

According to another embodiment of this aspect, the multiparticulate sprinkle dosage form is suitable for administration in intact form.

According to one embodiment of this aspect, the multiparticulate sprinkle dosage form is suitable for administration to a patient via a feeding tube.

Another embodiment of this aspect provides a method of administering multiparticulate sprinkle dosage form comprising (a) providing a multiparticulate sprinkle dosage form in the form of discrete units coated with an enteric polymer (b) sprinkling the discrete units on soft food, and (c) administering the soft food orally.

According to another embodiment, the multiparticulates when sprinkled on soft food are stable for at least 60 minutes.

A fourth aspect of the present invention provides a multiparticulate sprinkle dosage form comprising duloxetine or a pharmaceutically acceptable salt thereof, suitable for administration to a patient via enteral feeding tube such as NG tube or G tube, and has high acid resistance as compared to the marketed duloxetine delayed release capsules available under the brand name Cymbalta®.

According to one embodiment of this aspect, the multiparticulates have higher acid resistance stability after recovery through a combination of a syringe and the feeding tube.

According to another embodiment of this aspect, the multiparticulates when exposed to a liquid medium for 60 minutes in a syringe, and then passed through the NG tube into dissolution medium (0.1N HCl) followed by flushing with additional liquid medium, release not more than 5% of 1-naphthol impurity after 2 hours when placed in 1000 mL of 0.1 N HCl at 100 rpm in USP apparatus I.

According to another embodiment of this aspect, the multiparticulates when exposed to a liquid medium for 60 minutes in a syringe, and then passed through the NG tube into dissolution medium (0.1N HCl) followed by flushing with additional liquid medium, release not more than 10% of total duloxetine after 2 hours when placed in 1000 mL of 0.1 N HCl at 100 rpm in USP apparatus I.

Another embodiment of this aspect provides a method of administering multiparticulate sprinkle dosage form comprising duloxetine or a pharmaceutically acceptable salt thereof to a patient, comprising (a) providing a multiparticulate sprinkle dosage form in the form of discrete units coated with an enteric polymer, (b) dispersing the discrete units in a recommended volume of liquid medium placed in a syringe, (c) attaching the syringe to the feeding tube and delivering the contents through the feeding tube into the stomach, (d) flushing the feeding tube with an additional liquid medium to clear the tube.

The term "duloxetine", as used herein, refers to duloxetine and pharmaceutically acceptable salts thereof, including hydrates and solvates thereof, and crystalline or amorphous forms thereof. The preferred form is the hydrochloride salt.

The term "multiparticulate sprinkle dosage form" or "formulation" or "composition", as used herein, refer to plurality of physically discrete units, wherein each unit contains a predetermined quantity of active ingredient in association with pharmaceutically acceptable excipients. The dosage form used herein may be selected from conventional hard capsule (e.g. a capsule of gelatin, HPMC or a starch derivative), an easy to open capsule, or sachet. The multiparticulate sprinkle dosage form can provide dosage of about 10 mg, 20 mg, 30 mg, 40 mg, 50 mg, 60 mg, 70 mg, 80 mg, 90 mg, 100 mg, 110 mg, or 120 mg per dose or per day.

The term "multiparticulate" as used herein refers to plurality of physically discrete units, wherein each discrete unit is coated with an enteric polymer. The discrete unit comprises a drug core in the form of pellets, beads, particles, granules, or minitablets. In the present specification, the term "multiparticulates", "discrete units", "pellets", "beads", are used interchangeably.

The term "stable", as used herein, refers to a physical stability which means that the enteric coat over the multiparticulate units retain its structural integrity and does not rupture in a significant way after exposure to acidic environment for the given time period as determined by the drug release or 1-naphthol release in 0.1N HCl.

The term "about", as used herein, refers to any value which lies within the range defined by a variation of up to ±10% of the value.

The term "pharmaceutically acceptable excipients", as used herein, includes excipients that may be added in the multiparticulate sprinkle dosage form.

The term "cushioning agent" as used herein encompasses inert substances that provide flexibility to cores coated with enteric polymer such that when exposed to acidic environment for prolonged period, the enteric coat substantially retain their structural integrity and do not rupture in a significant way. Also the cushioning agent protects the enteric coat from damage due to accidental crushing or chewing of the pellets in the mouth.

The multiparticulate sprinkle dosage form comprises discrete units coated with an enteric polymer. The discrete units are drug cores covered with an enteric polymer. The drug core may comprise an inert core coated with a drug layer comprising drug and one or more pharmaceutically acceptable excipients. Alternatively, the drug core comprises the drug and one or more pharmaceutically acceptable excipients which are uniformly mixed. The inert core comprises sugar spheres or pellets of microcrystalline cellulose. The drug i.e. duloxetine hydrochloride is present in an amount of not less than about 10%, not less than about 15%, not less than about 20%, based on the total weight of the dosage form. Preferably, the drug i.e. duloxetine hydrochloride is present in an amount of about 20%, based on the total weight of the dosage form. The particle size of the active defined as $D_{90}$ is not more than 50 µm, preferably not more than 20 µm. For example, a multiparticulate sprinkle dosage form comprises: (a) an inert core, (b) a drug layer, and (c) an enteric coating layer over the drug coated core. A seal coat may optionally be present between the inert core and the drug layer (inner seal coat), between the drug layer and the enteric layer (sub coat), or above the enteric layer (finishing layer).

The multiparticulate sprinkle dosage form may be present in the form of easy to open capsules, conventional hard capsules (e.g. a capsule of gelatin, HPMC or a starch derivative), or a sachet.

The multiparticulate sprinkle dosage form comprises one or more pharmaceutically acceptable excipients selected from one or more of fillers, binders, disintegrants, lubricants, glidants, antiadherents, cushioning agents, and mixtures thereof.

Suitable diluents are selected from the group consisting of lactose, microcrystalline cellulose, starch, pregelatinized starch, calcium sulphate, calcium carbonate, powdered cellulose, mannitol, sorbitol, xylitol, lactitol, magnesium carbonate, dicalcium phosphate, tricalcium phosphate, calcium sulphate; and mixtures thereof.

Suitable binders are selected from the group consisting of cellulose derivatives (for example methylcellulose, hydroxypropyl cellulose, hydroxypropylmethyl cellulose, ethylcellulose, hydroxyl ethyl cellulose, L-hydroxy propyl cellulose); polyvinylpyrrolidone (for example povidone, copovidone); starch (for example corn starch, pre-gelatinized starch and hydroxypropyl starch); polymethacrylates (for example Eudragit RS, RL); and mixtures thereof.

Suitable disintegrants are selected from the group consisting of low substituted hydroxypropyl cellulose, crospovidone, croscarmellose sodium, starch derivatives; and mixtures thereof.

Suitable lubricants are selected from the group consisting of magnesium stearate, calcium stearate, zinc stearate; stearic acid, hydrogenated vegetable oil, hydrogenated castor oil, glyceryl palmitostearate, glyceryl behenate, polyethylene glycols, corn starch, sodium stearyl fumarate, sodium benzoate, mineral oil, talc, and mixtures thereof.

Suitable glidants or antiadherents are selected from the group consisting of talc, colloidal silicon dioxide, magnesium trisilicate, powdered cellulose, starch, tribasic calcium phosphate; and mixtures thereof.

Suitable cushioning agents are selected from the group comprising polyethylene glycols, polyoxyethylenes, colloidal and/or amorphous silicon dioxide, microcrystalline cellulose, polyvinyl acetate, waxes, fats, lipids, gums, and mixtures thereof. Examples of waxes include carnauba wax, bees wax, sperm whale wax, etc. Examples of fats and lipids include lecithin, hydrogenated vegetable oils, hydrogenated castor oil, hydrogenated sesame oil, etc., Examples of gums include gum arabica, xanthan gum, gum acacia, etc. It was surprisingly found that the use of cushioning agent in the dosage form imparts mechanical stability to the dosage form and aids in increase of the acid resistance of the dosage form. The cushioning agents may be layered over the drug cores or the enteric coat or the seal coat; or may be present in the drug cores or in the enteric coat or in the seal coat. Preferably, the cushioning agent is present in the outer finishing layer in an amount of not less than 20% and not more than 80% based on the weight of the coating layer. The cushioning agent is present in an amount of not less than 2% and not more than 25%, not more than 20%, not more than 15%, not more than 10% based on the total weight of the dosage form. Preferably, the cushioning agent is present in an amount of not less than 2% and not more than 25%, more preferably in an amount of about 5% based on the total weight of the dosage form.

The enteric coating layer comprises an enteric polymer and one or more pharmaceutically acceptable excipients. Suitable enteric polymers are selected from the group comprising of methacrylic acid copolymers, cellulose acetate phthalate, cellulose acetate succinate, polymethacrylic acid/ acrylic acid copolymer, hydroxypropyl methylcellulose phthalate, polyvinyl acetate phthalate, hydroxyethyl ethyl cellulose phthalate, cellulose acetate tetrahydrophthalate, acrylic resin, and mixtures thereof. The enteric polymer is present in an amount of more than 60%, or more than 70%, or more than 75% based on the total weight of the enteric coating layer, e.g. about 75% to about 98% by weight hydroxypropylmethylcellulose phthalate based on the total weight of the enteric coating layer. The enteric layer is present in an amount of at least about 15%, or at least about 18% by weight based on the weight of the core subunit without the enteric coat. Preferably, the enteric layer is present in an amount of about 15 to about 30%, or in an amount of about 18% to about 25% by weight based on the weight of the core subunit without the enteric coat. More preferably, the enteric layer is present in an amount of about 21%, about 23%, about 25% by weight based on the weight of the core subunit without the enteric coat. The thickness of enteric coating layer is between 30 μm to 50 μm.

The seal coating layer is optional. The seal coating layer comprises a film forming polymer and one or more pharmaceutically acceptable excipients. Additional excipients present in the coating include one or more of film forming polymers, plasticizers, anti-adherents, opacifiers, colorants, pigments, antifoaming agents, and polishing agents.

Suitable film-forming polymers are selected from the group consisting of hydroxypropylmethyl cellulose, ethyl cellulose, methyl cellulose, hydroxyethyl cellulose, hydroxypropyl cellulose, sodium carboxymethyl cellulose, cellulose acetate, hydroxypropyl methyl cellulose phthalate, cellulose acetate trimellitate, and methacrylic acid copolymers, e.g., Eudragit®, polyvinylpyrrolidone, polyvinylalcohol, polyethylene glycol, and mixtures thereof. Other suitable film-forming polymers which are known in the art may also be used. Many suitable film coating products which are commercially available, e.g., Opadry® and Opaglos® may be used.

Suitable plasticizers are selected from the group consisting of propylene glycol, triethyl citrate, tributyl citrate, dibutyl sebacate, acetyl tributyl citrate, glyceryl monostearate, triacetin, polyethylene glycol, diethyl phthalate, acetylated monoglycerides, diacetylated monoglycerides, cetyl alcohol, and mixtures thereof.

Suitable anti-adherents are selected from the group consisting of talc, magnesium stearate, fumed silica, and mixtures thereof.

Suitable opacifiers are selected from the group consisting of titanium dioxide, manganese dioxide, iron oxide, silicon dioxide, and mixtures thereof.

Suitable coloring agents are selected from FDA approved colorants such as iron oxide, lake of tartrazine, allura red, titanium dioxide, and mixtures thereof.

Suitable polishing agents are selected from the group consisting of polyethylene glycols of various molecular weights or mixtures thereof, talc, surfactants (glycerol monostearate and poloxamers), fatty alcohols (stearyl alcohol, cetyl alcohol, lauryl alcohol and myristyl alcohol), waxes (carnauba wax, candelilla wax and white wax), and mixtures thereof.

Various solvents that may be employed during the preparation of the dosage form of the present invention are selected from the group consisting of water, methyl alcohol, ethyl alcohol, isopropyl alcohol, n-butyl alcohol, acetone, acetonitrile, chloroform, methylene chloride, water, and mixtures thereof.

The coating may be carried out by using any conventional coating techniques known in the art, such as spray coating in a conventional coating pan or fluidized bed processor, or dip coating.

The multiparticulate sprinkle dosage form was opened and the multiparticulates multiparticulates were sprinkled on soft food. After a set contact time (90 minutes for acidic food and 60 minutes for alkaline food), the multiparticulates were assayed for the drug content. The assay results indicated that the drug content of the multiparticulates was maintained upon exposure to food indicating that the food did not affect the stability of the enteric coating.

The multiparticulate sprinkle dosage form was further evaluated for acid resistance by evaluating the drug release and impurity release when dissolution was carried out in acidic medium for 6 hours. In the presence of acid, duloxetine undergoes acid hydrolysis leading to formation of 1-naphthol impurity, phenolic impurity and Impurity E among which 1-naphthol is toxic in nature. Compared with the prior art, the dosage form provided better acid resistance for a longer period. When the dissolution was carried out on the present multiparticulate sprinkle dosage forms and the marketed delayed release capsules in 0.1N HCl dissolution medium for 6 hours using apparatus I at 100 rpm, the data clearly showed significant difference among the acid resistance of present dosage forms and the marketed delayed release capsules at 4 hours and 6 hours. The multiparticulate sprinkle dosage forms have higher acid resistance as compared to the marketed delayed release capsules.

The multiparticulate sprinkle dosage form has high acid resistance after 4 hours such that, when placed in 1000 mL of 0.1N HCl dissolution medium, not more than 5%, not more than 4%, not more than 3%, not more than 2%, not more than 1% of 1-naphthol impurity is released after 4 hours, when dissolution is carried out using USP apparatus I at 100 rpm.

The multiparticulate sprinkle dosage form has high acid resistance after 4 hours such that, when placed in 1000 mL of 0.1N HCl dissolution medium in USP apparatus I at 100 rpm, not more than 20%, not more than 15%, not more than 10%, not more than 8%, not more than 5% of duloxetine is released after 4 hours.

The multiparticulate sprinkle dosage form has high acid resistance after 4 hours such that, when placed in 1000 mL of 0.1N HCl dissolution medium in USP apparatus I at 100 rpm, not more than 30%, not more than 25%, not more than 20%, not more than 15%, or not more than 10% of total duloxetine is released after 4 hours.

The multiparticulate sprinkle dosage form has high acid resistance after 6 hours such that, when placed in 1000 mL of 0.1N HCl dissolution medium in USP apparatus I at 100 rpm, not more than 20%, not more than 18%, not more than 16%, not more than 10%, not more than 8% of 1-naphthol impurity is released after 6 hours.

The multiparticulate sprinkle dosage form has high acid resistance after 6 hours such that, when placed in 1000 mL of 0.1N HCl dissolution medium in USP apparatus I at 100 rpm, not more than 50%, not more than 45%, not more than 40%, not more than 35% of total duloxetine is released after 6 hours.

The multiparticulate sprinkle dosage form is resistant to alcohol induced dose dumping wherein the amount of the active agent released in alcoholic dissolution medium is less than the amount of active agent released from a commercially equivalent formulation. In order to quantify the resistance to ethanol-induced dose dumping, a dissolution test was performed in 5%, 20%, and 40% ethanolic HCl (FDA Guidelines) for two hours.

The multiparticulate sprinkle dosage forms are resistant to ethanol-induced dumping wherein not more than 90%, of duloxetine is released from the dosage form in 40% ethanol after 0.25, 0.5, 0.75, 1, 1.25, 1.5, 1.75, or 2 hours.

The multiparticulate sprinkle dosage forms are resistant to ethanol-induced dumping such that not more than 20%, 50%, 75%, 80%, preferably not more than 10%, 40%, 60%, 70%, more preferably not more than 5%, 30%, 50%, 70% of duloxetine is released from the dosage form in 20% ethanol after 0.75, 1, 1.25, 1.5 hours respectively. The amount of duloxetine released in 20% alcohol from the multiparticulate sprinkle dosage form is lower as compared to the amount of active agent released by the commercially equivalent formulation when exposed to the same concentration of ethanol for the same period.

The multiparticulate sprinkle dosage form is suitable for administration to pediatrics, geriatrics, patients with swallowing difficulties i.e. dysphagic patients as well as for patients with feeding tubes in place. The multiparticulate sprinkle dosage forms are suitable for administration as sprinkle dosage form as well as via enteral feeding tubes such as NG tube and G tube. The dosage form is also suitable for administration as intact capsules.

The present invention covers method of administering duloxetine to a patient, comprising (a) providing a multiparticulate sprinkle dosage form in the form of discrete units coated with an enteric polymer (b) sprinkling the discrete units on soft food, and (c) administering the soft food orally.

The multiparticulates can be placed in contact with soft food before administration without affecting the stability of the enteric coating. The multiparticulates when sprinkled on acidic soft food are stable for about 90 minutes, and when sprinkled on alkaline soft food having pH more than 5 are stable for about 60 minutes. In other words, the permitted hold time of the dosage form in contact with soft food before administration is at least 30 minutes, preferably at least 60 minutes. The permitted hold time of the dosage form in contact with soft food before administration is about 60 minutes for alkaline soft foods and about 90 minutes for acidic soft foods. The soft foods can have a pH ranging from 3.0 to 7.0. The acidic soft food have pH less than or equal to 5 and are selected from apple sauce, mango pudding, yoghurt or cheese. The alkaline soft foods have pH more than 5 and are selected from chocolate pudding, chocolate sauce or vanilla pudding.

The size of discrete units suitable to be sprinkled on soft food is less than 2 mm, preferably less than 1.5 mm.

The multiparticulates can be placed in contact with soft food of varying pH prior to administration. In case the food has acidic pH and the multiparticulates after placing in contact with food are not administered immediately and have a hold time before administration, the multiparticulates are then exposed to acidic environment in-vitro for additional time period in addition to exposure to acidic environment in stomach. Since, the sprinkle dosage form may undergo prolonged exposure to acidic environment in-vitro, hence they should have higher acid resistance as compared to the duloxetine delayed release formulations which are not suitable for administration with food. The multiparticulate sprinkle dosage form has higher acid resistance upon exposure to soft food as compared to the marketed duloxetine delayed release capsules available under the brand name Cymbalta®.

The acid resistance study of the sprinkle dosage form is carried out by placing the discrete units in contact with soft food for a defined time period followed by the dissolution testing, wherein dissolution is carried out in 1000 mL of 0.1N HCl in USP apparatus I at 100 rpm for 2 hours followed by pH 6.8 phosphate buffer in USP apparatus I at 100 rpm.

The multiparticulates when subjected to dissolution testing, after placing in contact with acidic soft food (soft food having pH less than or equal to 5) for 90 minutes, release 1-naphthol impurity in an amount of not more than 2%, not more than 1%, not more than 0.5%, not more than 0.2%, after 2 hours, when dissolution is carried out in 0.1N HCl.

The multiparticulates when subjected to dissolution testing, after placing in contact with alkaline soft food (soft food having pH more than 5) for 30 minutes, release 1-naphthol impurity in an amount of not more than 2%, not more than 1%, not more than 0.5%, not more than 0.2% after 2 hours, when dissolution is carried out in 0.1N HCl.

The multiparticulates when subjected to dissolution testing, after placing in contact with alkaline soft food for 30 minutes, release total duloxetine in an amount of not more than 12%, not more than 10%, not more than 8%, not more than 6% after 2 hours, when dissolution is carried out in 0.1N HCl.

The multiparticulates when subjected to dissolution testing, after placing in contact with alkaline soft food for 60 minutes, release 1-naphthol impurity in an amount of not more than 4%, not more than 3%, not more than 2%, not more than 1% after 2 hours, when dissolution is carried out in 0.1N HCl.

The multiparticulates when subjected to dissolution testing, after placing in contact with alkaline soft food for 60 minutes, release total duloxetine in an amount of not more than 12%, not more than 10%, not more than 8%, not more than 6% after 2 hours, when dissolution is carried out in 0.1N HCl.

The multiparticulate sprinkle dosage forms are also suitable for administration to a patient via enteral feeding tubes such as NG-tube or G-tube to patients who cannot safely swallow or are unable to take medication orally. The enteral feeding tube may be a NG-tube 3.5-16 French or a G-tube of 12-28 French. Successful delivery of sprinkle drug products through an enteral feeding tube requires that all of the beads (uncrushed) be able to safely pass through the feeding tube and not cause tube occlusions.

The multiparticulate sprinkle dosage forms can be suspended in a suitable vehicle, preferably water and administered via enteral feeding tube. For patients who have a feeding tube in place, duloxetine multiparticulate dosage form is administered by a method comprising: (a) providing a multiparticulate sprinkle dosage form in the form of discrete units coated with an enteric polymer, (b) dispersing the discrete units in a recommended volume of liquid medium placed in a syringe, (c) attaching the syringe to the feeding tube and delivering the contents through the feeding tube into the stomach, (d) flushing the feeding tube with an additional liquid medium to clear the tube.

The multiparticulate sprinkle dosage forms are suitable for administration through a NG-tube or G-tube of at least 12 French. The multiparticulates do not adhere on the walls of the tube. The enteric coat of the discrete units remains stable after passage through the enteral feeding tube. The multiparticulate dosage forms have higher acid resistance stability as compared to the marketed duloxetine delayed release capsules after recovery through a combination of syringe and the feeding tube.

The multiparticulate sprinkle dosage form when exposed to a liquid medium for 60 minutes in a syringe, and then passed through the NG tube into dissolution medium (0.1N HCl) followed by flushing the syringe with an additional liquid medium, releases not more than 15%, not more than 10%, not more than 5%, or not more than 2%, or not more than 1%, not more than 0.5%, or not more than 0.2% of 1-naphthol impurity after 2 hours when dissolution is carried out in 1000 mL of 0.1N HCl in USP apparatus I at 100 rpm.

The multiparticulate sprinkle dosage form when exposed to a liquid medium for 60 minutes in a syringe, and then passed through the NG tube into dissolution medium (0.1N HCl) followed by flushing the syringe with an additional liquid medium, releases not more than 30%, not more than 20%, not more than 15%, not more than 10%, or not more than 5%, or not more than 2% of total duloxetine after 2 hours when dissolution is carried out in 1000 mL of 0.1N HCl in USP apparatus I at 100 rpm.

A relative bioavailability study was carried out in healthy fasting subjects, by administering duloxetine multiparticulate dosage form after sprinkling on soft food and comparing them to marketed duloxetine hydrochloride delayed release capsules available under the brand name Cymbalta®. Further, the food affect and impact of soft food on the bioavailability of the formulations was evaluated.

The multiparticulate sprinkle dosage form is bioequivalent to the marketed delayed release formulation available under the brand name Cymbalta®. Further the dosage form is substantially free of food effect.

While carrying out the bioavailability studies, It was surprisingly found that the multiparticulate sprinkle dosage form show slightly higher relative rate of absorption. The pharmacokinetic data indicate that the multiparticulate sprinkle dosage form when administered after sprinkling on soft food has about 14% higher relative rate (Cmax) and about 10% higher relative extent of absorption (AUC) as compared to the reference product Cymbalta® administered as intact capsules. Hence, it is believed that there exists a possibility of dose reduction without impacting the relative bioavailability of duloxetine from its multiparticulate sprinkle dosage form.

The multiparticulate sprinkle dosage form can be administered orally at a low dose and may provide equivalent efficacy in comparison to the duloxetine delayed release formulation marketed under the trade name Cymbalta®. The low dose is at least 5%, at least 10%, at least 15%, at least 20%, at least 25%, at least 30%, at least 35%, or at least 40% lower than currently approved dose of marketed delayed release capsules.

The multiparticulate sprinkle dosage form may be used for the treatment of disease or condition requiring duloxetine therapy.

The present invention is illustrated below by reference to the following examples. However, one skilled in the art will appreciate that the specific methods and results discussed are merely illustrative of the invention, and not to be construed as limiting the invention, as many variations thereof are possible without departing from the spirit and scope of the invention.

Manufacturing Procedure:
1. Drug layering: Hydroxypropylmethyl cellulose was dissolved in purified water, duloxetine hydrochloride and talc were suspended into the solution, and the solution was sprayed on sugar spheres to obtain drug loaded pellets.
2. Sub coating: Hydroxypropylmethyl cellulose and sucrose were dissolved in purified water and talc was suspended into the solution, and the solution was sprayed on to the drug loaded pellets of step 1.
3. Enteric coating: Hydroxypropylmethyl cellulose phthalate and triethyl citrate were dissolved in mixture of acetone and purified water, talc was suspended into the solution, and solution was sprayed on to sub-coated pellets of step 2.
4. Finishing layer: Hydroxypropylmethyl cellulose was dissolved in purified water; talc, titanium dioxide, polyethylene glycol (if present) were suspended into the solution, and the solution was sprayed on to the enteric loaded pellets of step 3.
5. The top coated pellets of step 5 were filled in the capsule.

Examples 3, 4 and 5

| S. N. | Ingredients | Example 3 Quantity (mg/capsule) | Example 4 Quantity (mg/capsule) | Example 5 Quantity (mg/capsule) |
|---|---|---|---|---|
| | DRUG LAYERED PELLETS | | | |
| 1 | Sugar Spheres | 105 | 105 | 105 |
| 2 | Duloxetine Hydrochloride equivalent to Duloxetine base 60 mg | 67.36 | 67.36 | 67.36 |

Examples 1 and 2

| S. N. | Ingredients | Example 1 Quantity (mg/capsule) | Example 2 Quantity (mg/capsule) |
|---|---|---|---|
| | DRUG LAYERED PELLETS | | |
| 1 | Sugar Spheres | 105 | 105 |
| 2 | Duloxetine Hydrochloride equivalent to Duloxetine base 60 mg | 67.36 | 67.36 |
| 3 | Hydroxypropylmethyl cellulose | 6.72 | 6.72 |
| 4 | Talc | 3.36 | 3.36 |
| 5 | Purified water | q.s | q.s |
| | SUB COATING | | |
| 6 | Hydroxypropylmethyl cellulose | 7.83 | 7.830 |
| 7 | Sucrose | 15.64 | 15.64 |
| 8 | Talc | 31.27 | 31.27 |
| 9 | Purified water | q.s. | q.s. |
| | ENTERIC COATING (21% weight gain) | | |
| 10 | Hydroxypropylmethyl cellulose Phthalate (HP 50)-dissolves a pH of less than or equal to 5.0 at 37 C. or 25 C. | 40.15 | 40.15 |
| 11 | Triethyl Citrate | 4.00 | 4.00 |
| 12 | Talc | 5.66 | 5.66 |
| 13 | Purified water | q.s. | q.s. |
| 14 | Acetone | q.s. | q.s. |
| | FINISHING LAYER | | |
| 15 | Hydroxypropylmethyl cellulose | 5.74 | 18.41 |
| 16 | Titanium Dioxide | 2.87 | 5.14 |
| 17 | Talc | 2.87 | 5.14 |
| 18 | Purified water | q.s. | q.s. |
| 19 | Polyethylene glycol (PEG 6000) | 17.22 | — |

-continued

Examples 3, 4 and 5

| S. N. | Ingredients | Example 3 Quantity (mg/capsule) | Example 4 Quantity (mg/capsule) | Example 5 Quantity (mg/capsule) |
|---|---|---|---|---|
| 3 | Hydroxypropylmethyl cellulose | 6.72 | 6.72 | 6.72 |
| 4 | Talc | 3.36 | 3.36 | 3.36 |
| 5 | Purified water | q.s | q.s | q.s |
| | SUB COATING | | | |
| 6 | Hydroxypropylmethyl cellulose | 7.83 | 7.83 | 7.83 |
| 7 | Sucrose | 15.64 | 15.64 | 15.64 |
| 8 | Talc | 31.27 | 31.27 | 31.27 |
| 9 | Purified water | q.s. | q.s. | q.s. |
| | ENTERIC COATING (23%/25% weight gain) | | | |
| 10 | Hydroxypropylmethyl cellulose Phthalate (HP 50) | 47.79 | 47.79 | 43.97 |
| 11 | Triethyl Citrate | 4.77 | 4.77 | 4.37 |
| 12 | Talc | 6.74 | 6.74 | 6.19 |
| 13 | Purified water | q.s. | q.s. | q.s. |
| 14 | Acetone | q.s. | q.s. | q.s. |
| | FINISHING LAYER | | | |
| 15 | Hydroxypropylmethyl cellulose | 5.93 | 19.02 | 5.83 |
| 16 | Titanium Dioxide | 2.97 | 5.31 | 2.91 |
| 17 | Talc | 2.97 | 5.31 | 2.91 |
| 18 | Purified water | q.s. | q.s. | q.s. |
| 19 | Polyethylene glycol (PEG 6000) | 17.78 | — | 17.59 |

Manufacturing Procedure:

The capsules of Examples 3, 4 and 5 were prepared by following the same procedure as for Examples 1 and 2.

Acid Resistance Studies

The multiparticulate sprinkle capsules of Examples 1, 2 and 4 were compared with the marketed delayed release Cymbalta® DR capsules for the release profile in acidic media (0.1N HCl 1000 mL) using USP apparatus I at 100 rpm and were found to have the following release profile:

TABLE 1

| Product | % 1-Naphthol | Phenolic Impurity | Impurity E | % Duloxetine | % Total Duloxetine Release |
|---|---|---|---|---|---|
| Release after 4 hours in 0.1N HCl | | | | | |
| Cymbalta® | 7.0 | 9.0 | 0.0 | 24.0 | 40.0 |
| Example 1 | 1.0 | 2.0 | 0.0 | 4.0 | 8.0 |
| Example 2 | 3.0 | 6.0 | 0.0 | 7.0 | 16.0 |
| Example 4 | 1.0 | 2.0 | 0.0 | 2.0 | 5.0 |
| Release after 6 hours in 0.1N HCl | | | | | |
| Cymbalta® | 16.0 | 24.0 | 1.0 | 19.0 | 60.0 |
| Example 1 | 7.0 | 9.0 | 0.0 | 16.0 | 32.0 |
| Example 2 | 16.0 | 19.0 | 0.0 | 23.0 | 58.0 |
| Example 4 | 8.0 | 10.0 | 0.0 | 22.0 | 40.0 |

As is evident from the above data (Table 1), the test product has higher acid resistance than the reference product. The undesirable 1-naphthol impurity formation is also lower than the reference product.

Alcohol Dose Dumping Studies

The multiparticulate sprinkle capsules of Examples 2 and 4 were compared with the marketed delayed release Cymbalta® DR capsules for the release profile in 1000 mL alcoholic media (0.1N HCl with 5%/20%/40% alcohol) using USP apparatus I at 100 rpm and were found to have the following release profile:

TABLE 2

% Duloxetine release in alcoholic media.

| Dissolution medium | Product | % Duloxetine Release Time (minutes) | | | | | | | |
|---|---|---|---|---|---|---|---|---|---|
| | | 15 | 30 | 45 | 60 | 75 | 90 | 105 | 120 |
| 0.1N HCl + 5% alcohol | Example 2 | 1 | 0 | 1 | 0 | 0 | 1 | 1 | 2 |
| | Example 4 | 0 | 0 | 0 | 0 | 0 | 0 | 0 | 0 |
| | Cymbalta® | 1 | 0 | 0 | 0 | 0 | 0 | 0 | 1 |
| 0.1N HCl + 20% alcohol | Example 2 | 0 | 1 | 16 | 44 | 71 | 79 | 78 | 70 |
| | Example 4 | 0 | 0 | 3 | 27 | 48 | 68 | 79 | 74 |
| | Cymbalta® | 2 | 1 | 27 | 71 | 79 | 80 | 76 | 73 |
| 0.1N HCl + 40% alcohol | Example 2 | 31 | 73 | 88 | 95 | 96 | 95 | 91 | 90 |
| | Example 4 | 31 | 71 | 80 | 85 | 85 | 87 | 87 | 87 |
| | Cymbalta® | 27 | 85 | 91 | 92 | 92 | 92 | 90 | 89 |

As is evident from the above data in Table 2, the test product has higher alcohol resistance than the reference product, especially in 20% alcoholic media.

Soft Food Study—Drug Assay

The sprinkle capsules of Example 2 and 4 and Cymbalta® were opened and contents were sprinkled on soft food. After 90 minute contact time, the sample was analyzed for the drug content.

TABLE 3

% Assay after contact with soft food

| Soft food | Contact time | Product | % Assay (Duloxetine) |
|---|---|---|---|
| 5 g Apple sauce | 90 minutes | Example 2 | 99 |
| | | Example 4 | 98.8 |
| | | Cymbalta® | 99.2 |
| Chocolate pudding | 30 minutes | Example 2 | 97.1 |
| | | Example 4 | 97.3 |
| | | Cymbalta® | 95.8 |
| Chocolate pudding | 60 minutes | Example 2 | 96.1 |
| | | Example 4 | 96.3 |
| | | Cymbalta® | 95.9 |

As is evident from the above data in Table 3, the multiparticulate sprinkle capsules of present invention are stable for 90 minutes when placed in contact with acidic soft food and are stable for 60 minutes when placed in contact with alkaline soft food.

Soft Food Study—Dissolution Study

The sprinkle capsule of Example 1 and Cymbalta® capsule were opened and pellets were sprinkled on soft food. After defined contact time, dissolution study was carried out in 1000 mL of 0.1N HCl for 2 hours followed by 1000 mL of pH 6.8 phosphate buffer using USP Apparatus I (Basket) at 100 rpm. The test product was compared with the marketed delayed release formulation of duloxetine for the release profile. The results are presented in Tables 4 and 5.

TABLE 4

Comparative dissolution profile for Duloxetine capsules of Example 2 (Test A),
Example 4 (Test B) and Cymbalta ® (Reference) after exposure of pellets to 2 g Yoghurt
for 90 minutes:

| Product | Acid Stage 0.1N HCl (pH 1.2) 2 hours | | | | | Buffer stage (pH 6.8 phosphate buffer) | | | | |
|---|---|---|---|---|---|---|---|---|---|---|
| | % Phenolic Impurity | % Duloxetine impurity E | % Duloxetine | % 1-Naphthol | % Duloxetine Dissolved | 15 min | 30 min | 45 min | 60 min | 90 min |
| Example 2 | 0 | 0 | 2 | 0 | 2 | 46 | 69 | 78 | 83 | 89 |
| Example 4 | 1 | 0 | 0 | 0 | 1 | 54 | 74 | 83 | 88 | 93 |
| Cymbalta ® | 1 | 0 | 1 | 0 | 1 | 15 | 39 | 57 | 70 | 81 |

As is evident from the above data in Table 4, the test products are stable when placed in contact with acidic soft food for 90 minutes.

TABLE 5

Comparative dissolution profile for Duloxetine capsules of Example 1 (Test)
and Cymbalta ® (Reference) after exposure of pellets to chocolate pudding for
30 minutes and 60 minutes:

| Contact time | Product | Acid Stage 0.1N HCl (pH 1.2) 2 hours | | | | | Buffer stage (pH 6.8 phosphate buffer) | | | | |
|---|---|---|---|---|---|---|---|---|---|---|---|
| | | % Phenolic Impurity | % Impurity E | % Duloxetine | % 1-Naphthol | % Duloxetine Dissolved | 15 min | 30 min | 45 min | 60 min | 90 min |
| 30 minutes | Example 1 | 2 | 0 | 3 | 0 | 5 | 18 | 27 | 37 | 48 | 59 |
| | Cymbalta ® | 6 | 0 | 4 | 3 | 12 | 31 | 50 | 62 | 69 | 79 |
| 60 minutes | Example 1 | 2 | 0 | 1 | 1 | 5 | 19 | 28 | 38 | 51 | 66 |

As is evident from the above data in Table 6, the test product compared to Cymbalta is more stable when placed in contact with alkaline soft food for 60 minutes.

In-Vitro Nasogastric (NG) Tube Studies

The sprinkle capsules of Example 2 and 4 and Cymbalta® DR capsules were opened and contents were emptied in a syringe containing 50 mL water and kept for 60 minutes. The contents of syringe were then passed through 12 French NG-tube into the 925 mL of dissolution media (0.1N HCl). The syringe was flushed by additional 25 mL water into the dissolution medium and dissolution test was carried out in 0.1N HCl in USP apparatus I at 100 rpm for 2 hours. The test products were compared with the marketed delayed release formulation of duloxetine for the release profile after exposure to syringe and NG tube. The results are given in Table 6:

TABLE 6

Comparative dissolution profile for sprinkle capsules of
Example 1 (Test A), Example 2 (Test B), Example 4 (Test C) and
Cymbalta ® (Reference) after exposure of
pellets to syringe and NG-tube:

| Product | % 1-Naphthol | % Phenolic Impurity | % Duloxetine | Impurity E | % Total Duloxetine Release |
|---|---|---|---|---|---|
| Cymbalta ® 60 mg | 21.0 | 32.0 | 20.0 | 1.0 | 74.0 |
| Example 1 | 1.0 | 1.0 | 3.0 | 0.0 | 5.0 |
| Example 2 | 1.0 | 0.0 | 3.0 | 0.0 | 4.0 |
| Example 4 | 0.0 | 0.0 | 1.0 | 0.0 | 1.0 |

As is evident from the above data in Table 6, the test products show significant protection against formation of 1-naphthol impurity as compared to the reference product.

Pharmacokinetic Studies Under Fasting Conditions

The multiparticulate sprinkle capsules of Example 2 and Example 4 were compared with Cymbalta® delayed release capsules under fasting condition with contents sprinkled over applesauce in 12 healthy adult human subjects.

Values for various pharmacokinetic parameters, including observed $C_{max}$, $AUC_{0-t}$ and $AUC_{0-\infty}$ were calculated and are provided in Table 7 below.

Reference (R): Cymbalta® capsules 60 mg
Test (A): Duloxetine multiparticulate sprinkle capsule 60 mg (Example 4)
Test (B): Duloxetine multiparticulate sprinkle capsule 60 mg (Example 2)

TABLE 7

Comparative Pharmacokinetic data for Duloxetine sprinkle capsules of Example 2 (Test A) and Example 4 (Test B) and Cymbalta ® (R) in healthy adult human subjects:

| | Test B vs Reference | | | Test A vs Reference | | |
|---|---|---|---|---|---|---|
| | In $C_{max}$ | In $AUC_{0-t}$ | In $AUC_{0-inf}$ | In $C_{max}$ | In $AUC_{0-t}$ | In $AUC_{0-inf}$ |
| Ratio T/R (%) | 114.21 | 109.57 | 109.60 | 109.99 | 106.43 | 106.23 |
| 90% Confidence Interval | 97.46-133.84 | 93.29-128.69 | 93.61-128.33 | 93.85-128.89 | 90.61-125.00 | 90.73-124.39 |

Average $T_{max}$ values for Test B, Test A and Reference are 5 hours, 5 hours and 4.5 hours, respectively, which indicate a comparable absorption pattern.
Average $T_{lag}$ values for Test B, Test A and Reference are 0.67 hours, 0.75 hours and 0.91 hours, respectively, which indicate a comparable delayed release pattern.
The extent of drug absorption (AUC) was comparable between the test products and reference products.

As is evident from the above data in Table 7, the test products when sprinkled on applesauce and administered orally are bioequivalent to the reference product administered intact.

The invention claimed is:

1. A multiparticulate sprinkle dosage form comprising a plurality of discrete units, wherein each unit comprises:
   (a) a core subunit comprising a drug layered subunit surrounding an inert core, wherein the drug layer comprises duloxetine or a pharmaceutically acceptable salt thereof; and
   (b) an enteric coating layer surrounding the core subunit; wherein each unit further comprises a finishing layer containing a cushioning agent, surrounding the enteric coating layer, wherein the cushioning agent is selected from the group consisting of polyethylene glycol, polyoxyethylene, polyvinyl acetate and gum; wherein not more than 90% of duloxetine is released from the dosage form when place in 40% ethanol in 0.1 NHCl for 2 hours.

2. The multiparticulate sprinkle dosage form according to claim 1, wherein the core subunit further comprises a sub-coating layer formed by a film forming agent selected from the group consisting of hydroxypropyl cellulose, hydroxypropylmethyl cellulose, and ethylcellulose.

3. The multiparticulate sprinkle dosage form according to claim 1, wherein the enteric coating layer comprises about 75% to about 99% by weight of an enteric polymer, based on the weight of the enteric coating.

4. The multiparticulate sprinkle dosage form according to claim 1, wherein the polyethylene glycol having a molecular weight of 6000 is present in an amount of about 2% to about 20% based on the total weight of the dosage form.

5. The multiparticulate sprinkle dosage form according to claim 1, wherein the dosage form contains duloxetine or pharmaceutically acceptable salts thereof in an amount of about 20% by weight of the dosage form.

6. The multiparticulate sprinkle dosage form according to claim 3, wherein the enteric polymer is selected from the group consisting of methacrylic acid copolymers, cellulose acetate phthalate, cellulose acetate succinate, polymethacrylic acid, hydroxypropyl methyl cellulose, hydroxypropyl methylcellulose phthalate, polyvinyl acetate phthalate, hydroxyethyl ethyl cellulose phthalate, cellulose acetate tetrahydrophthalate, acrylic resin, and mixtures thereof.

7. The multiparticulate sprinkle dosage form according to claim 1, wherein the discrete units are in the form selected from the group consisting of pellets, beads, particles, granules, and minitablets.

* * * * *